United States Patent
Reissmann

(10) Patent No.: US 7,481,222 B2
(45) Date of Patent: Jan. 27, 2009

(54) DEVICE FOR ARTIFICIAL RESPIRATION WITH AN ENDOTRACHEAL TUBE

(75) Inventor: Hajo Reissmann, Keplerstrasse 11, D-22765 Hamburg (DE)

(73) Assignee: Hajo Reissmann, Hamburg (DE)

( * ) Notice: Subject to any disclaimer, the term of this patent is extended or adjusted under 35 U.S.C. 154(b) by 0 days.

(21) Appl. No.: 10/477,263

(22) PCT Filed: May 8, 2002

(86) PCT No.: PCT/EP02/05118

§ 371 (c)(1),
(2), (4) Date: Jun. 8, 2004

(87) PCT Pub. No.: WO02/089885

PCT Pub. Date: Nov. 14, 2002

(65) Prior Publication Data

US 2004/0231673 A1    Nov. 25, 2004

(30) Foreign Application Priority Data

May 10, 2001 (DE) .............................. 101 23 278

(51) Int. Cl.
*A61M 16/00* (2006.01)
(52) U.S. Cl. ................... 128/207.14; 128/911; 128/912
(58) Field of Classification Search ..................
128/207.14–207.18, 200.24, 200.28, 206.26,
128/911, 912; 604/93.01, 96.01, 98.01, 102.01,
604/118, 119, 128; 600/531
See application file for complete search history.

(56) References Cited

U.S. PATENT DOCUMENTS

| 2,318,518 | A |   | 5/1943 | Opperer | ................... 4/246.1 |
| 3,102,537 | A |   | 9/1963 | Bartlett, Jr. | ............. 128/201.13 |
| 3,871,373 | A | * | 3/1975 | Jackson | ................. 128/203.27 |
| 3,912,795 | A | * | 10/1975 | Jackson | ..................... 261/36.1 |
| 4,048,993 | A | * | 9/1977 | Dobritz | ................. 128/201.13 |
| 5,040,532 | A | * | 8/1991 | Alfery | .................... 128/207.15 |
| 5,207,220 | A | * | 5/1993 | Long | ..................... 128/207.14 |
| 5,309,906 | A | * | 5/1994 | LaBombard | ........... 128/207.14 |
| 5,372,131 | A | * | 12/1994 | Heinen, Jr. | ............. 128/207.15 |
| 5,582,167 | A | * | 12/1996 | Joseph | .................... 128/207.15 |
| 5,706,830 | A | * | 1/1998 | Parker | .................... 128/203.12 |
| 5,740,796 | A | * | 4/1998 | Skog | ..................... 128/204.23 |
| 6,166,092 | A | * | 12/2000 | Sekins et al. | ................. 514/772 |

(Continued)

FOREIGN PATENT DOCUMENTS

DE            25 35 191          2/1977

(Continued)

*Primary Examiner*—Steven O Douglas
(74) *Attorney, Agent, or Firm*—Alston & Bird LLP

(57) ABSTRACT

A device for ventilation, comprising
a ventilator for providing a stream of gas for ventilation at an outlet,
a hose for inspiration air one end of which is connected to the outlet,
a double-lumen endotracheal tube one lumen of which, at its end distal to the patient, is connected to the other end of the hose for inspiration air,
flow meters for measuring the streams of gas in the two lumina of the endotracheal tube,
pressometers for measuring the pressures at the ends distal to the patient of the two lumina,
an evaluation means for determining the flow resistance in a lumen flowed through by gas because of the stream of gas measured therein and the pressures measured, and
a means for outputting an information about the flow resistance of the lumina.

27 Claims, 2 Drawing Sheets

U.S. PATENT DOCUMENTS

| | | | |
|---|---|---|---|
| 6,272,933 B1 * | 8/2001 | Gradon et al. | 73/861 |
| 6,390,092 B1 * | 5/2002 | Leenhoven | 128/204.23 |
| 6,390,988 B1 * | 5/2002 | Robinson | 600/531 |
| 6,502,572 B1 * | 1/2003 | Berthon-Jones et al. | 128/204.23 |
| 6,510,841 B1 * | 1/2003 | Stier | 123/472 |
| 6,533,730 B2 * | 3/2003 | Strom | 600/533 |
| 6,598,602 B1 * | 7/2003 | Sjoholm | 128/200.16 |
| 6,626,169 B2 * | 9/2003 | Gaitini | 128/200.14 |
| 6,840,241 B2 * | 1/2005 | Strom | 128/204.21 |

FOREIGN PATENT DOCUMENTS

| | | |
|---|---|---|
| DE | 195 28 113 | 2/1997 |
| EP | 0 806 217 A2 | 11/1997 |

\* cited by examiner

DEVICE FOR ARTIFICIAL RESPIRATION WITH AN ENDOTRACHEAL TUBE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The invention relates to a device for ventilation via an endotracheal tube.

The predominant majority of patients being ventilated during an intensive-care therapy or anaesthesia have their airway secured by an endotracheal tube. To this end, an endotracheal tube which consists of a plastic or rubber tube, as a rule, is introduced into the trachea through the mouth or nose or by a making an incision in the trachea ("tracheotomy"). At the tracheal end, the endotracheal tube mostly is provided with a inflatable endotracheal tube "cuff" which seals the trachea, permits ventilation at an excess pressure, and protects the airways from the penetration of foreign matter. The end distal to the patient of the endotracheal tube is coupled to a ventilation device via a hose system. At the point of transition from the endotracheal tube to the hose system, there is an Y connection piece which has connected thereto an inspiratory hose and an expiratory hose or expiratory valve leading to the atmosphere.

A respiratory air filter can be disposed between the endotracheal tube and the hose system to minimize the exchange of micro-organisms and other contaminants between the patient and hose system. The extension of time intervals between the exchanges of the hose which becomes possible thereby is advantageous both economically and ecologically. Further, heat-and-moisture exchangers may be provided between the hose system and the endotracheal tube which cause the inspiration air to be humidified to prevent the patient's airways from becoming parched. This is accomplished by condensing the moisture contained in the expiration air on specific filter-like materials and re-evaporating the moisture during the succeeding inspiration. Further, there is a so-called "active humidification" via a heated evaporator in the inspiratory hose of the hose system.

The lungs effect an exchange of gas with the external air in a pendular process. At this stage, whenever an inspiration takes place gas which has been left behind from prior expiration in the so-called "dead space" first gets into the lungs. The dead space is the entirety of all air conductors which are flowed through during both inspiration and expiration. It comprises the bronchi and trachea as well as the conventionally single-lumen endotracheal tube and any preceding breathing air filters or heat-to-moisture exchangers. It ends in an Y-connector which ramifies the airway for inspiration and expiration.

The respiratory excursions subject the lungs to mechanical loads and require the spontaneously breathing patient to do breathing effort. Since the dead space (both anatomical and device-related) can constitute a significant percentage of the respiratory stroke (about 30% to more than 50%) its minimization is an important step towards reducing such loads and breathing effort fractions. A known action to reduce the dead space is to insert an endotracheal tube having two lumina (a "double-lumen endotracheal tube") which are separately connected to the inspiratory hose and expiratory hose or the expiratory valve leading to the atmosphere. A ventilation system having a double-lumen endotracheal tube is described in DE 25 35 191 A1, for example. In a double-lumen endotracheal tube, a separator for the inspiration and expiration legs of the ventilation device is installed in lieu of a connection piece for the two lumina. It is located deeply in the trachea at the tracheal end of the endotracheal tube. Accordingly, this reduces the dead space of the system and the breathing effort which caused by the dead space.

Another advantage of double-lumen endotracheal tubes is provided when there is a pressure-regulating ventilation. During such a ventilation, the ventilator aims at regulating the pressure at the Y connection piece. To this end, the common ventilators do not carry out a pressure tap which is separately led up to the Y connection piece because the pressure prevailing there can be measured just as well via the upright gas column of the hose which is just not flowed through during the respective respiratory phase. When a double-lumen endotracheal tube is used the Y connection piece and, hence, the regulation point will be shifted into the trachea. As a direct consequence, the patient need no longer overcome that part of breathing effort which is caused by the flow resistances in a single-lumen endotracheal tube. The task of overcoming the flow resistances of the double-lumen endotracheal tube is automatically imposed on the ventilator.

When the endotracheal tube kinks or foreign matter such as secretions from the trachea settle(s) in its interior its resistance will increase. This can cause a hazard to the patient because it will impede its ventilation and/or high pressures will build up in the lungs (with restriction being preponderant to expiration). Since such changes occur to the portion of the endotracheal tube that cannot be seen in a visual inspection only late signs will be noticed, i.e. reductions to ventilation or pressure rises.

These disadvantages can be overcome to a limited extent by monitoring the pressure at the Y connection piece and the gas flows. However, such monitoring cannot discriminate or associate the mechanical properties of the structures beyond the Y connection piece (filter, endotracheal tube, airways, lungs, surrounding tissue, muscle activity). Therefore, monitoring the tube properties is only possible to a very limited extent and only major changes are detected, if at all.

Another problem is posed by the necessity for constant humidification of the patient's inspiration air because the endotracheal tube keeps it away from the natural humidifiers (the mucosae of the nose and pharynx). Heat-and-moisture exchangers, as a rule, simultaneously function as filters, thus forming a contaminant barrier between the patient and the hose system. However, they require to be alternately flowed through by expiration and inspiration air to satisfy their function. Therefore, they cannot be employed for double-lumen endotracheal tubes. At present, if double-lumen endotracheal tubes are used it is only possible to actively humidify such air by means of electrically heated evaporators.

Another problem is how to remove secretions and foreign matter from the endotracheal tube. While a ventilation therapy is performed the natural cleaning mechanism of the airways is capable of transporting secretions and foreign matter into the trachea up to the endotracheal tube, if at all. They have to be drawn off not later than from this point. To this end, it is usual to disconnect the Y connection piece from the endotracheal tube so permit a suction catheter to be introduced into the endotracheal tube. This interrupts ventilation and any continuously positive airway pressure (CPAP) or positive end-expiratory pressure (PEEP), which is a common prophylaxis against the collapse of diseased parts of the lung, cannot be maintained. Therefore, special inflation manoeuvres become necessary after this suction to re-open collapsed parts of the lungs.

Furthermore, it has been known already to introduce the suction catheter through a particular angled adapter, which forms a seal around the catheter, between the endotracheal tube and the Y connection piece. The ventilator remains connected to the endotracheal tube and ventilation can be continued, on a principle. However, problems will arise by the fact that the portion of the lumen that is responsible for ventilation is reduced in dependence on the dimensions of the endotracheal tube and suction catheter and, as a consequence, its resistance to both inspiration and expiration air is more or less increased. Recent studies have shown that continuing a volume-controlled ventilation should be avoided in any case under these circumstances: Hazardous positive or negative pressures are possible, which depend on the pattern of ventilation and the different dimensions of the hose. Therefore, if ventilation is to be continued under a suction this has definitely to be done in a pressure-regulated mode. Even then, if a conventional single-lumen endotracheal tube is used the pressure in the trachea will always be distinctly below the target pressure setting during a suction because there is the endotracheal tube with its reduced lumen between the trachea and the Y connection piece, the point of measurement and regulation.

DE 195 28 113 A discloses a ventilation device for the controlled mechanical ventilation of patients including a measurement and evaluation of the expiratory time constant of the respiratory system. Characteristic changes of the time constant-to-volume relationship are supposed to allow the detection and differentiation of elevated resistances or obstructions of the endotracheal tube, on one hand, and those of the trachea and bronchi, on the other.

GB 2 318 518 discloses a double-lumen endotracheal tube in which one lumen serves for the supply of a continuous flow of fresh gas and the larger lumen serves for discontinuous expiration. Controlled ventilation is effected by a phased closure of the larger lumen. The expiration limb of the device has connected thereto a pressure sensor.

U.S. Pat. No. 3,102,537 A discloses a respiration device with a face mask, particularly for air and space travel, which ensures improved transfer of moisture from the expired air to the inspired air and a maximum saving of oxygen or another inspired gas from an external source. A common wall permeable to moisture is disposed between the expiration and the inspiration air conduit. In addition, there is a reservoir which is passed in by a first portion of the expired gas in order to be inspired first during the following inspiration.

BRIEF SUMMARY OF THE INVENTION

Accordingly, it is the object of the invention to provide an operatively improved device for ventilation via an endotracheal tube.

The object is achieved by a device for ventilation having
a ventilator for providing a stream of gas for respiration at an outlet,
a hose for inspiration air one end of which is connected to the outlet,
a double-lumen endotracheal tube one lumen of which is distally connected to the other end of the inspiratory hose,
flow meters connected to the ends distal to the patient of the two lumina for measuring the streams of gas in the two lumina of the endotracheal tube,
pressometers connected to the ends distal to the patients of the two lumina for measuring the pressures at the ends distal to the patient of the two lumina,
an evaluation means for determining the flow resistance in a lumen which is flowed through by gas on the basis of the stream of gas measured therein and the pressures measured, and
a means to output an information about the flow resistance of the lumina.

The invention relies on the possibility of determining the flow resistance in the lumen which is flowed through by gas from the values measured for the stream of gas resistance in the lumen which is flowed through by gas and the pressures prevailing at the two lumina. Namely, the pressometer connected to the end distal to the patient of the lumen which is flowed through by gas measures the pressure directly at the end distal to the patient of this lumen and the pressometer connected to the end distal to the patient of the lumen which is not flowed through by gas measures the pressure at the tracheal end of the lumen which is flowed through so that the pressure loss of the lumen which is flowed through results from the two pressures. Then, the flow resistance of the lumen which is flowed through can be calculated, along with the stream of gas passing through the lumen which is flowed through. For this purpose, reference is made to the interconnections known from the fluid mechanics between the pressure loss, volumetric flow, and flow resistance coefficient of tubes which are flowed through. The flow resistance, in turn, allows to directly conclude therefrom whether the endotracheal tube is inadmissibly kinked or clogged so that corrective actions are required. In a software-controlled device for ventilation, the evaluation and display procedures described can be easily implemented under a software control.

The rule for all of the inventive devices for ventilation is that the lumen for expiration may be connected to the atmosphere via a valve, preferably an actively controlled valve, or may be connected to an inlet of the ventilator for expired breathing air via an expiratory hose. The former may be the case particularly for emergency ventilators. It is common specifically for anaesthesia ventilation that the expired air is returned to the ventilator if gases which are relatively expensive are fed to the ventilation system and a recovery of the gases from the ventilation system is beneficial.

The flow meters and/or pressometers can be located on the ventilator and/or at the end of the tracheal tube. Preferably, they are on the ventilator because if they were disposed at the end of the tracheal tube they would make it more difficult to handle them. If the expiratory end of the endotracheal tube is not connected to the ventilator via an expiratory hose it is obligatory to arrange the flow meter and pressometer of the expiratory end on the endotracheal tube. Also in such case, however, it is preferred to locate the flow meter and pressometer of the inspiratory end in the ventilator.

Basically, the device determines the flow resistance of the lumen which is flowed through by gas and the hose connected thereto towards the ventilator. If the properties of the hose with no endotracheal tube are known to the device it can determine the flow resistance of the endotracheal tube. For a determination of the properties of the hose, it can be disconnected from the endotracheal tube and can be opened to the atmosphere or two hoses can be connected to each other and be flowed through by streams of gas. If the hose is opened to the atmosphere the pressure loss can be determined by means of the ambient pressure, which is known, and the pressure measured at one hose end and the stream of gas which was measured. When the hoses are connected to each other the pressures measured at the ends of the hoses are incorporated into the calculation. Preferably, there are valve means between the endotracheal tube and the hose/hoses to connect the hose/hoses to the environment and/or to each other.

An embodiment of the device has
an endotracheal tube and
at least one membrane permeable to water in a wall between two lumina of the endotracheal tube and/or between two hoses for connecting the endotracheal tube to a ventilator.

The moisture from the expired air condenses on the side of the water-permeable membrane that forms part of the expiration air limb in order to be re-absorbed by the dry inspired air on the other side of the membrane that forms part of the limb for inspiration air. Since the exchange of moisture takes place in a counter-current it can become highly effective if suitable dimensions are chosen. Efficiency can be improved by heating the stream of gas in the limb for inspiration air because warm gas will take up moisture more rapidly and better. Likewise, it is possible to enhance efficiency by using a membrane material which preferably transports water from the expiratory limb to the inspiratory limb. Such "asymmetric" materials are known to be used in sanitary products (sanitary towels or baby's diapers), for example. A large exchange surface can also be achieved by causing the hoses and/or lumina of a double-lumen endotracheal tube to envelope each other, e.g. by surrounding each other concentrically.

It can also be beneficial to combine the second solution with the first solution. This also applies to any aspects of the first and second solutions.

According to an aspect, the device for ventilation has
a ventilator for providing a stream of gas for ventilation at an outlet,
a hose for inspiration air one end of which is connected to the outlet,
a double-lumen endotracheal tube one lumen of which is distally connected to the other end of the inspiratory hose,
pressometers for measuring pressures at the ends of the two lumina distal from the patient,
a closable opening at the distal end of the lumen for the expired stream of gas to sealingly introduce a suction catheter up to the tracheal end of this lumen, and
a means for regulating the pressure to a predetermined value in the lumen which is not flowed through by the gas.

Pressure-regulated ventilation via the double-lumen endotracheal tube may re readily continued under a suction with no positive or negative pressures occurring because the ventilation pressure is regulated just in the place where suction also makes itself felt, i.e. in the trachea. The means for pressure regulation is connected to the pressometers and controls the stream of gas. The ventilation pressure can further be controlled by a valve at the end distal to the patient of the lumen for expiration. The control of the pressure via the stream of gas presupposes that the inspiratory limb of the device, i.e. the hose and the lumen via which the stream of gas is fed for ventilation, does not exert too much resistance to the flow to prevent the ventilation device from building up the desired pressure in the trachea. Introduction of the suction catheter into the lumen through which the expiratory air is discharged avoids a disadvantageous increase in flow resistance in the other lumen.

It is preferred to additionally design the lumen for the expired stream of gas with a larger cross-section than has the lumen for the stream of gas für ventilation (asymmetric double-lumen endotracheal tube). The arrangement of the suction catheter could result in a reduction of expiration; however, this effect is alleviated or eliminated by the suction stream of gas which also causes some sort of expiration (passing by the ventilator). The pressure range predetermined by the user is not exited at any time in any case. For the first time, this allows to carry out a ventilation therapy during which the pressure never drops below the predetermined CPAP or PEEP (see above), even in connection with suction manoeuvres.

According to an aspect, the device for ventilation has
a ventilator to provide a stream of gas for ventilation at an outlet,
a hose for inspiration gas one end of which is connected to the outlet,
a double-lumen endotracheal tube one lumen of which is connected to the other end of the hose for inspiration gas at the end distal to the patient, and
a device for applying an oscillating pressure to the end distal to the patient of the endotracheal tube lumen connected to the hose for inspiration air.

Applying a high-frequency pressure oscillation to the inspiratory limb of the ventilator improves the exchange of gas with the patient. This allows to reduce the stream of gas for patient ventilation. In this context, "high-frequency" denotes frequencies which exceed the breathing frequency of the patients, particularly frequencies which amount to at least more than 5 Hz. The application of a high-frequency pressure oscillation has admittedly been known in connection with single-lumen endotracheal tubes. However, since the dead volume is considerable pressure fluctuations of a high energy have to be applied here to achieve an improvement to gas exchange. The provision of suitable oscillators poses a problem. When used in conjunction with a double-lumen endotracheal tube, an improvement to gas exchange is achieved already by means of oscillators which exhibit relatively low energies and amplitudes because the dead volume is reduced very much. The propagation of pressure fluctuations into the lungs can be enhanced by configuring the lumen for expiration as a low pass type for pressure oscillation. Preferably, the expiratory limb of the ventilation device contains an active valve the actuation of which is coordinated with the oscillation of the pressure generator.

BRIEF DESCRIPTION OF THE DRAWING

The invention will be described below with reference to the accompanying drawing which schematically shows an embodiment.

DETAILED DESCRIPTION OF THE INVENTION

Figure 1:
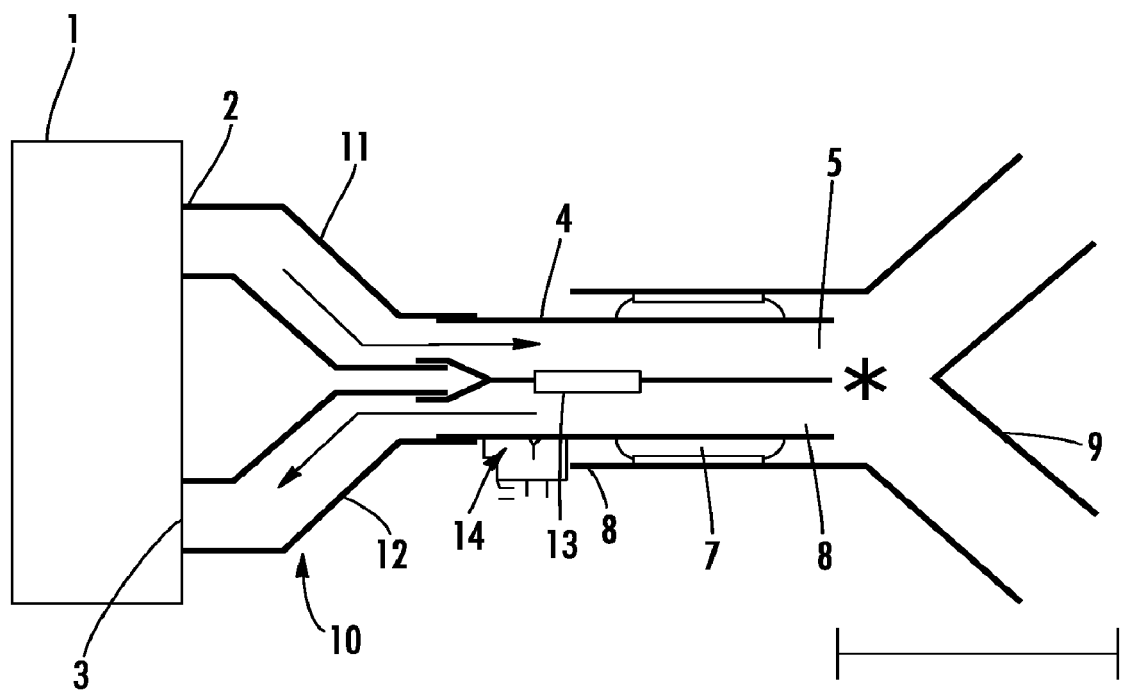
FIG. 1 is a schematic of an embodiment of the invention.

While this invention may be embodied in many different forms, there are described in detail herein a specific preferred embodiment of the invention. This description is an exemplification of the principles of the invention and is not intended to limit the invention to the particular embodiment illustrated.

The device for ventilation comprises a ventilator 1 with an outlet 2 at which a stream of gas is provided and an inlet 3 to which a stream of expired gas can be fed. At the inlet 3, the ventilator 1 has an active valve which is closed during inspiration in order to maintain the pressure in the lungs, and which is opened during expiration. Behind the valve, the expired gas can be released to the environment. Alternatively, the stream of expired gas can be prepared for reuse in the ventilator 1 (by removing the $CO_2$) and the gas needed for ventilation will be re-supplied to the outlet where fresh ventilation gas can be admixed.

Further, there is an endotracheal tube 4 which has two lumina 5, 6. At its tracheal end, this double-lumen endotracheal tube 4 has an inflatable cuff 7 which provides a seal towards a trachea 8, the endotracheal tube 4 being advanced up to a point just in front of the bronchi 9.

The ventilator 1 is connected to the end distal to the patient of the endotracheal tube 4 via a hose system 10. The hose system 10 has an inspiratory hose 11 which is connected to the outlet 2 and lumen 5. It further has an hose 12 for expiratory gas which is connected to the lumen 6 and inlet 3.

The ventilator 1 houses flow meters for measuring the streams of gas from the outlet 2 and into the inlet 3. The ventilator I also houses pressometers for measuring the pressure at the outlet 2 and inlet 3.

Using the aid of the gas flow and pressure values, a computer integrated in the ventilator calculates the flow resistance each in the lumens 5 and 6 which are just flowed through by gas. If admissible limit values are exceeded the endotracheal tube 4 is assumed to be kinked or clogged and an optical or acoustic signal is emitted.

Furthermore, the wall between the two lumina 5, 6 is designed as a membrane 13 which is permeable to water in an area. This membrane 13 causes moisture to be transmitted from the expiration air in the lumen 6 to the inspiration air in lumen 5.

Furthermore, the lumen 6 is closed by an opening 14 through which a suction catheter can be sealingly introduced, if required, up to the tracheal end of the endotracheal tube 4. Since the pressure is measured at the outlet 2 and inlet 3 and the streams of gas are regulated in the ventilator 1 the effect is that the pressure in the trachea is maintained at a constant level.

Finally, a means for generating a, pulsating pressure which has a frequency exceeding the breathing frequency can be disposed in the ventilator 1 and acts upon the outlet 2 to intensify the exchange of gas during ventilation.

Figure 2:
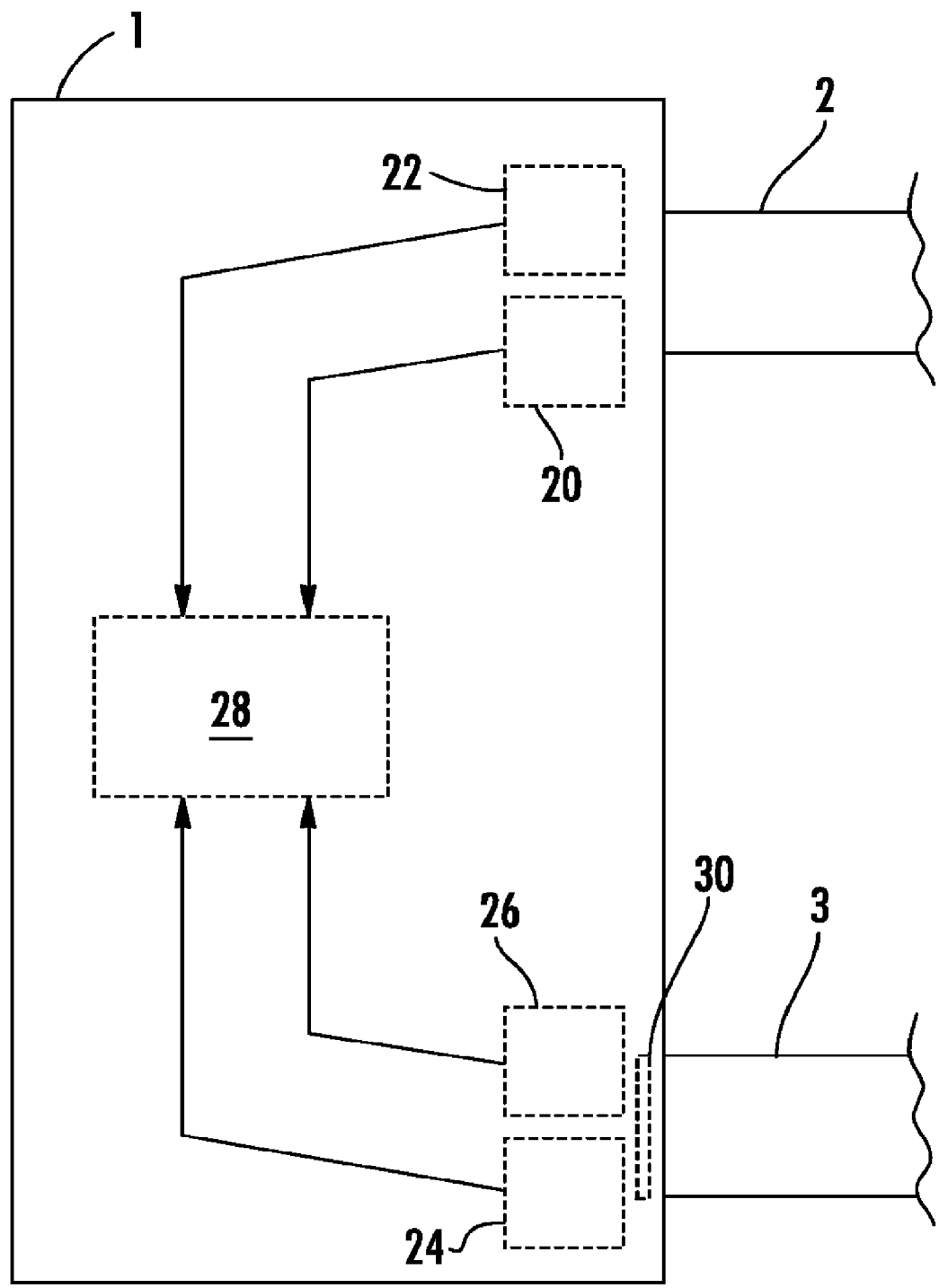
FIG. 2 is a schematic showing the flowmeters and pressometers, housed in ventilator 1, and also showing the computer, connected to the flowmeters and pressometers.

FIG. 2 schematically shows flowmeter 20 and pressometer 22, both shown in phantom, which are connected to outlet 2. Flowmeter 24 and pressometers 26, both shown in phantom, are connected to inlet 3. The flowmeters 20 and 24, and pressometers 22 and 26 are all connected to a computer 28, which determines the flow resistance in the lumens 5 and 6. The flowmeters 20 and 24 measure the gas flow in lumens 5 and 6, while the pressometers 22 and 26 measure the pressure in lumens 5 and 6.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A device for ventilation of a patient, the device comprising
    a ventilator having an outlet for providing a stream of gas for ventilation and an inlet for receiving a stream of expired gas,
    a double-lumen endotracheal tube having an end distal to the patient and a tracheal end that engages the patient's trachea, wherein, at the end distal to the patient, a lumen for inspiratory gas is connected to the ventilator outlet and a separate lumen for expiratory gas is connected to the ventilator inlet such that, during ventilation, a stream of gas is only flowing through one lumen at a time,
    a flow meter located at the end of the double-lumen endotracheal tube distal to the patient and connected to the inspiratory lumen and a separate flow meter located at the end of the double-lumen endotracheal tube distal to the patient and connected to the expiratory lumen, and
    a pressometer located at the end of the double-lumen endotracheal tube distal to the patient and connected to the inspiratory lumen and a separate pressometer located at the end of the double-lumen endotracheal tube distal to the patient and connected to the expiratory lumen, the pressometers being adapted for alternating between measuring the pressure directly at the end distal to the patient of the double-lumen endotracheal tube and the pressure at the tracheal end of the double-lumen endotracheal tube depending upon which lumen through which gas is flowing.

2. The device according to claim 1 wherein one or more of the flow meters or pressometers are integrated in the ventilator.

3. The device according to claim 1 comprising valve means located at the ventilator inlet for connecting the with one or both of the environment and the outlet.

4. The device according to claim 1, further comprising
    a closable opening at the end distal to the patient of the expiratory lumen to sealingly introduce a suction catheter up to the tracheal end of the endotracheal tube.

5. The device according to claim 1, further comprising a means for applying a high frequency oscillating pressure to the end distal to the patient of the inspiratory lumen.

6. The device according to claim 1, further comprising
    a computer for determining the flow resistance in the inspiratory lumen and the expiratory lumen, based on measurements from the flow meters and the pressometers.

7. The device according to claim 1, further comprising an evaluation means for determining the flow resistance in an individual lumen.

8. The device according to claim 1, further comprising a means for outputting an information about the flow resistance of the lumina.

9. The device according to claim 1, further comprising at least one membrane permeable to water in a wall between the inspiratory lumen and the expiratory lumen of the endotracheal tube.

10. The device according to claim 9, wherein the membrane passes water from the expired breath in the expiratory lumen to the inspiratory lumen.

11. The device according to claim 9, further comprising means for heating the stream of ventilation gas.

12. The device according to claim 9, wherein the membrane comprises a filter.

13. The device according to claim 1, wherein the endotracheal tube comprises an asymmetric endotracheal tube.

14. The device according to claim 13, wherein the expiratory lumen has a larger cross-section than the inspiratory.

15. The device according to claim 1, wherein one lumen of the endotracheal tube is enveloped by the other lumen of the endotracheal tube.

16. A method for determining the flow resistance of an endotracheal tube comprising:
 (a) providing a ventilation system comprising:
  (i) a ventilator having an outlet for providing a stream of gas for ventilation and an inlet to which a stream of expired gas is fed;
  (ii) a double-lumen endotracheal tube having an end distal to the patient and a tracheal end that engages the patient's trachea, wherein, at the end distal to the patient, a lumen for inspiratory gas is connected to the ventilator outlet and a separate lumen for expiratory gas is connected to the ventilator inlet such that, during ventilation, a stream of gas is only flowing through one lumen at a time;
  (iii) a flow meter located at the end of the double-lumen endotracheal tube distal to the patient and connected to the inspiratory lumen and a separate flow meter located at the end of the double-lumen endotracheal tube distal to the patient and connected to the expiratory lumen; and
  (iv) a pressometer located at the end of the double-lumen endotracheal tube distal to the patient and connected to the inspiratory lumen and a separate pressometer located at the end of the double-lumen endotracheal tube distal to the patient and connected to the expiratory lumen, the pressometers being adapted to alternate between measuring the pressure directly at the end distal to the patient of the double-lumen endotracheal tube and the pressure at the tracheal end of the double-lumen endotracheal tube depending upon which lumen through which gas is flowing;
 (b) calculating the flow of gas in one or both lumina;
 (c) calculating the pressure of the gas in one or both lumina; and
 (d) determining the flow resistance within the endotracheal tube based on the calculated gas flow and gas pressure.

17. The method of claim 16, wherein one or more of the flow meters and pressometers are located on the ventilator.

18. The method of claim 16, wherein the device further comprises evaluation means for determining the flow resistance within the endotracheal tube.

19. A method for increasing moisture content in air inspired by a patient through an endotracheal tube, the method comprising:
 (a) providing a ventilation system comprising:
  (i) a ventilator having an outlet for providing a stream of gas for ventilation;
  (ii) a double-lumen endotracheal tube, having an inspiratory lumen for transmission of the gas for ventilation from the ventilator and a separate expiratory lumen for transmission of air expired by the patient, the inspiratory lumen and the expiratory lumen being separated by a wall; and
  (iii) at least one membrane permeable to water located in the wall between the inspiratory lumen and the expiratory lumen of the endotracheal tube; and
 (b) initiating inspiration and expiration of air through the endotracheal tube such that moisture from the expired air condenses on the side of the membrane adjacent the expiratory lumen, the moisture exchanges through the membrane, and is re-absorbed in the inspiratory lumen by the stream of gas for ventilation provided by the ventilator.

20. The method of claim 19, further comprising heating the stream of gas in the inspiratory lumen.

21. The method of claim 19, wherein one lumen of the endotracheal tube is enveloped by the other lumen of the endotracheal tube.

22. A method of removing clogging matter from an endotracheal tube during intubation of a patient while maintaining tracheal pressure, the method comprising:
 (a) providing a ventilation system comprising:
  (i) a ventilator having an outlet for providing a stream of gas for ventilation and an inlet for receiving a stream of expired gas;
  (ii) a double-lumen endotracheal tube, having an end distal to the patient and a tracheal end that engages the patient's trachea, wherein, as the end distal to the patient, a lumen for inspiratory gas is connected to the ventilator outlet and a separate lumen for expiratory gas is connected to the ventilator inlet such that, during ventilation, a stream of gas is only flowing through one lumen at a time;
  (iii) a closable opening in the expiratory lumen;
  (iv) a flow meter located at the end of the endotracheal tube distal to the patient and connected to the inspiratory lumen and a separate flow meter located at the end of the endotracheal tube distal to the patient and connected to the expiratory lumen;
  (v) a pressometer located at the end of the endotracheal tube distal to the patient and connected to the inspiratory lumen and a separate pressometer located at the end of the endotracheal tube distal to the patient and connected to the expiratory lumen, the pressometers being adapted to alternate between measuring the pressure directly at the end distal to the patient of the endotracheal tube and the pressure at the tracheal end of the endotracheal tube depending upon which lumen through which gas is flowing; and
  (vi) evaluation means for determining the flow resistance in a lumen in relation to the gas flow and the gas pressure of the lumen;
 (b) sealingly introducing through the closable opening a device for removal of clogging matter in the expiratory lumen;
 (c) removing the clogging matter from the expiratory lumen; and
 (d) maintaining and regulating tracheal pressure by continuously evaluating gas flow and gas pressure and continuously increasing or decreasing the stream of gas provided by the ventilator to compensate for pressure changes arising from said removal of the clogging matter.

23. The method of claim 22, wherein step (d) comprises using the pressometer connected to the lumen through which gas is flowing to measure the gas pressure directly at the end distal to the patient of the lumen through which gas is flowing and using the pressometer connected to the lumen through which gas is not flowing to measure the gas pressure at the tracheal end of the lumen through which gas is flowing.

24. The method of claim 16, wherein step (c) comprises using the pressometer connected to the lumen through which gas is flowing to measure the gas pressure directly at the end distal to the patient of the lumen through which gas is flowing and using the pressometer connected to the lumen through which gas is not flowing to measure the gas pressure at the tracheal end of the lumen through which gas is flowing.

25. The method of claim 24, comprising using the gas pressure directly at the end distal to the patient of the lumen through which gas is flowing and the gas pressure at the tracheal end of the lumen through which gas is flowing to calculate the pressure loss of the lumen through which gas is flowing.

26. The method of claim 16, comprising alternating between determining flow resistance of the inspiratory lumen and the expiratory lumen of the double-lumen endotracheal tube.

27. The method of claim 16, comprising using the determined flow resistance to evaluate whether the endotracheal tube is kinked or clogged and whether corrective actions are required.

* * * * *